United States Patent
Castro et al.

(10) Patent No.: US 7,105,025 B2
(45) Date of Patent: *Sep. 12, 2006

(54) LOW PROFILE FUSION CAGE AND INSERTION SET

(75) Inventors: Salvatore Castro, Milford, MA (US); Christopher McDonnell, Sandy Hook, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/146,787

(22) Filed: Jun. 7, 2005

(65) Prior Publication Data

US 2005/0228499 A1    Oct. 13, 2005

Related U.S. Application Data

(60) Continuation of application No. 10/338,463, filed on Jan. 8, 2003, now Pat. No. 7,070,621, which is a division of application No. 09/545,320, filed on Apr. 7, 2000, now Pat. No. 6,783,545.

(60) Provisional application No. 60/128,113, filed on Apr. 7, 1999.

(51) Int. Cl.
*A61F 2/44* (2006.01)
*A61B 17/56* (2006.01)

(52) U.S. Cl. .................... 623/17.16; 623/17.11

(58) Field of Classification Search ... 623/16.11–17.11
See application file for complete search history.

(56) References Cited

U.S. PATENT DOCUMENTS 6,174,311 B1 * 1/2001 Branch et al. ............. 606/61

* cited by examiner

*Primary Examiner*—Thaomas Barrett
(74) *Attorney, Agent, or Firm*—Lerner, David, Littenberg, Krumholz & Mentlik, LLP

(57) ABSTRACT

A bone fusion implant system including a first implant body having substantially flat top and bottom surfaces for engaging opposing vertebrae and a side wall extending between the top and bottom surfaces, the side wall including a concave recess and a second implant body having substantially flat top and bottom surfaces for engaging the opposing vertebrae and a side wall extending between the top and bottom surfaces thereof, the side wall of the second implant including an arcuate portion adapted to be received within the concave recess for enabling the first and second implant bodies to be positioned in nested side-by-side relation between the opposing vertebrae.

13 Claims, 5 Drawing Sheets

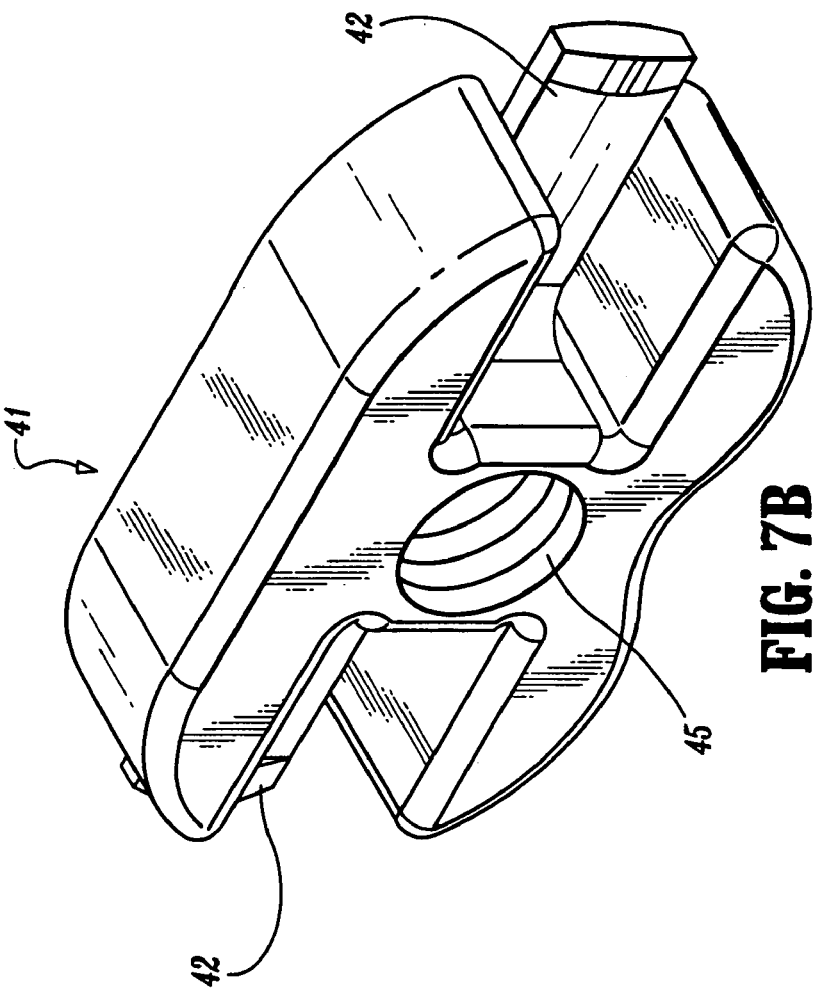
FIG. 7B
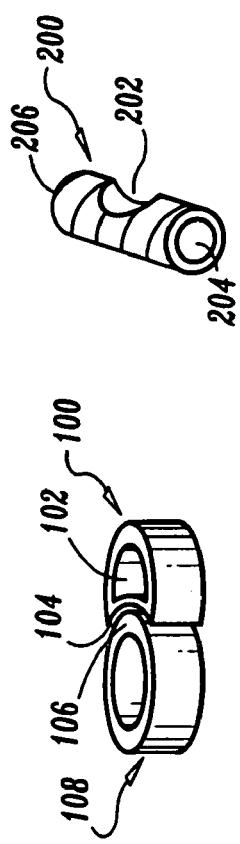
FIG. 9
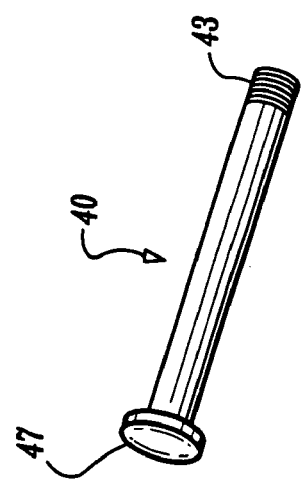
FIG. 8
FIG. 7A

LOW PROFILE FUSION CAGE AND INSERTION SET

CROSS REFERENCE TO RELATED APPLICATIONS

The present application is a continuation of U.S. patent application Ser. No. 10/338,463, filed Jan. 8, 2003 now U.S. Pat. No. 7,070,621, now allowed, which is a divisional of U.S. patent application Ser. No. 09/545,320, filed Apr. 7, 2000, now U.S. Pat. No. 6,783,545, which claims benefit of U.S. Provisional Application No. 60/128,113, filed Apr. 7, 1999. The disclosures of the '463, '320 and '113 applications are hereby incorporated by reference herein.

BACKGROUND OF THE INVENTION

The present application relates to a low profile fusion cage and an insertion set for the low profile fusion cage.

Known spinal implants, such as those used for vertebral fusion, are often used in pairs to provide adequate, evenly distributed support and fusion inducement. Because of limited space for implantation and for surgical maneuvering, it is sometimes difficult or unfeasible to implement a pair of implants that otherwise have desirable dimensions and attributes. Certain existing implant designs are configured for close, adjacent placement to other implants, but none achieve optimum performance, versatility or ease of insertion.

SUMMARY OF THE INVENTION

It is an object of the present invention to provide an implant design, and associated instruments and methods, that provide optimum configurations for placement of adjacent implants in close proximity with optimum performance. These objects and others are achieved through the present invention implant configuration and associated instruments and method.

In a preferred embodiment, a fusion implant according to the present invention is provided with a concave cut-away portion on a circumferential surface of an elongated implant. The concave portion accommodates the outer contour of an adjacently placed implant having a corresponding concave surface. A novel dual tang distractor tool is provided with two over-lapping cross-sectional configurations to facilitate close insertion and placement of implants according to the present invention.

BRIEF DESCRIPTION OF THE DRAWINGS

Preferred embodiments of the present disclosure are described herein with reference to the drawings wherein:

FIG. 7 is a perspective view of the plate of the impactor;

FIG. 8 is a front, perspective view of an alternative embodiment of the present invention; and FIG. 9 is a front, perspective view of another alternative embodiment of the present invention.

DETAILED DESCRIPTION OF THE PREFERRED EMBODIMENT

FIGS. 1–3*a* illustrate perspective, side and end views of the low profile fusion cage (10) of the present invention. The present invention cage (10) is of the type known commercially as the Ray TFC™ Fusion Cage currently marketed by Surgical Dynamics, Inc. The Ray TFC™ Fusion Cage is disclosed in commonly assigned U.S. Pat. No. 4,961,740, the contents of which are incorporated herein by reference.

Figure 1:
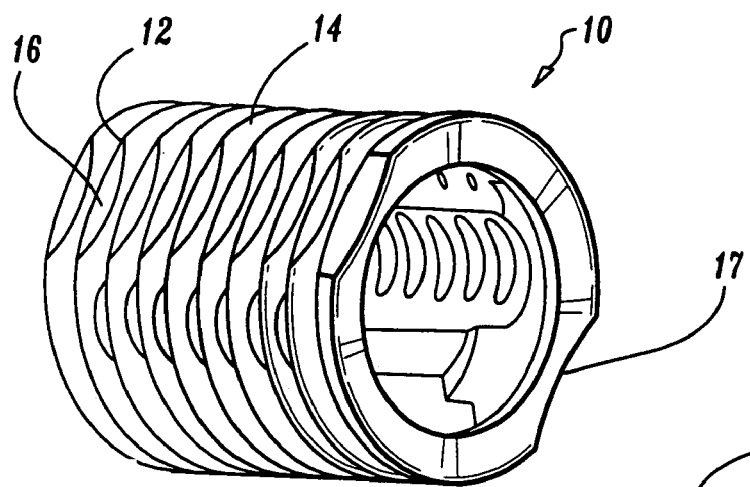
FIG. 1 is a perspective view of the fusion cage of the present disclosure.
Figure 2:
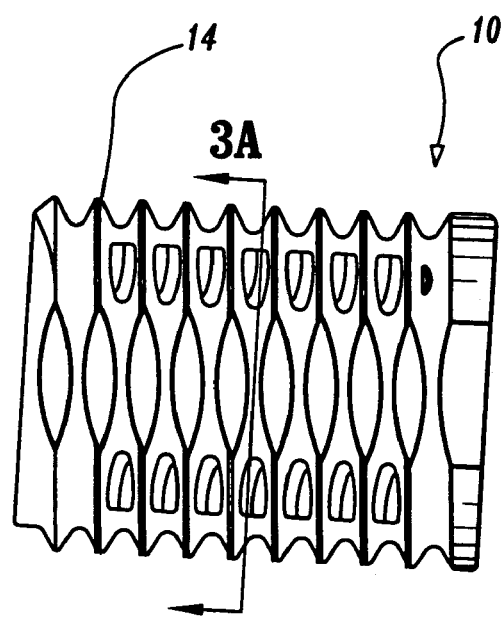
FIG. 2 is a side view of the fusion cage of FIG. 1.
Figure 3A:
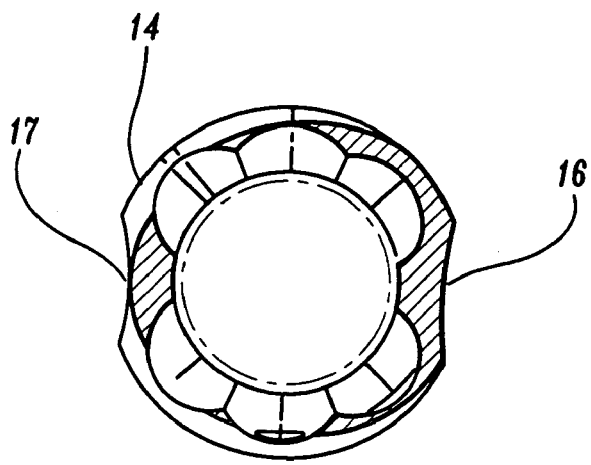
FIG. 3*a* is a cross-sectional view of the fusion cage taken along lines B—B of FIG. 1.
Figure 3B:
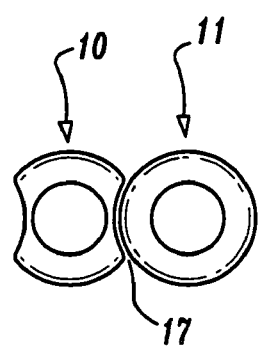
FIG. 3*b* is a cross-sectional view of the fusion cage as shown in FIG. 3*a*, with a conventional implant cage of similar view placed adjacently thereto.
Figure 4:
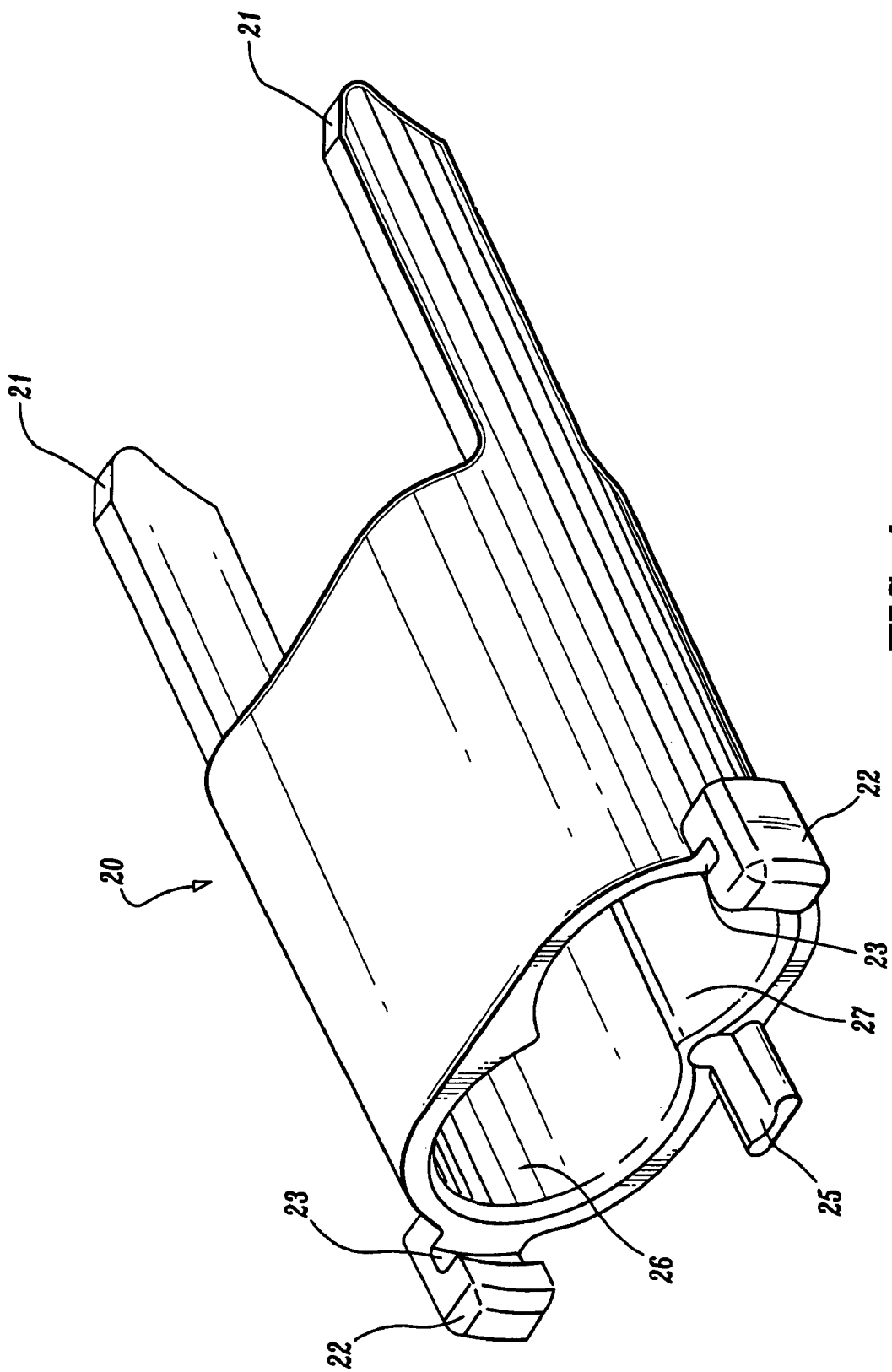
FIG. 4 is a perspective view of the tang retractor of the present disclosure.
Figure 5:
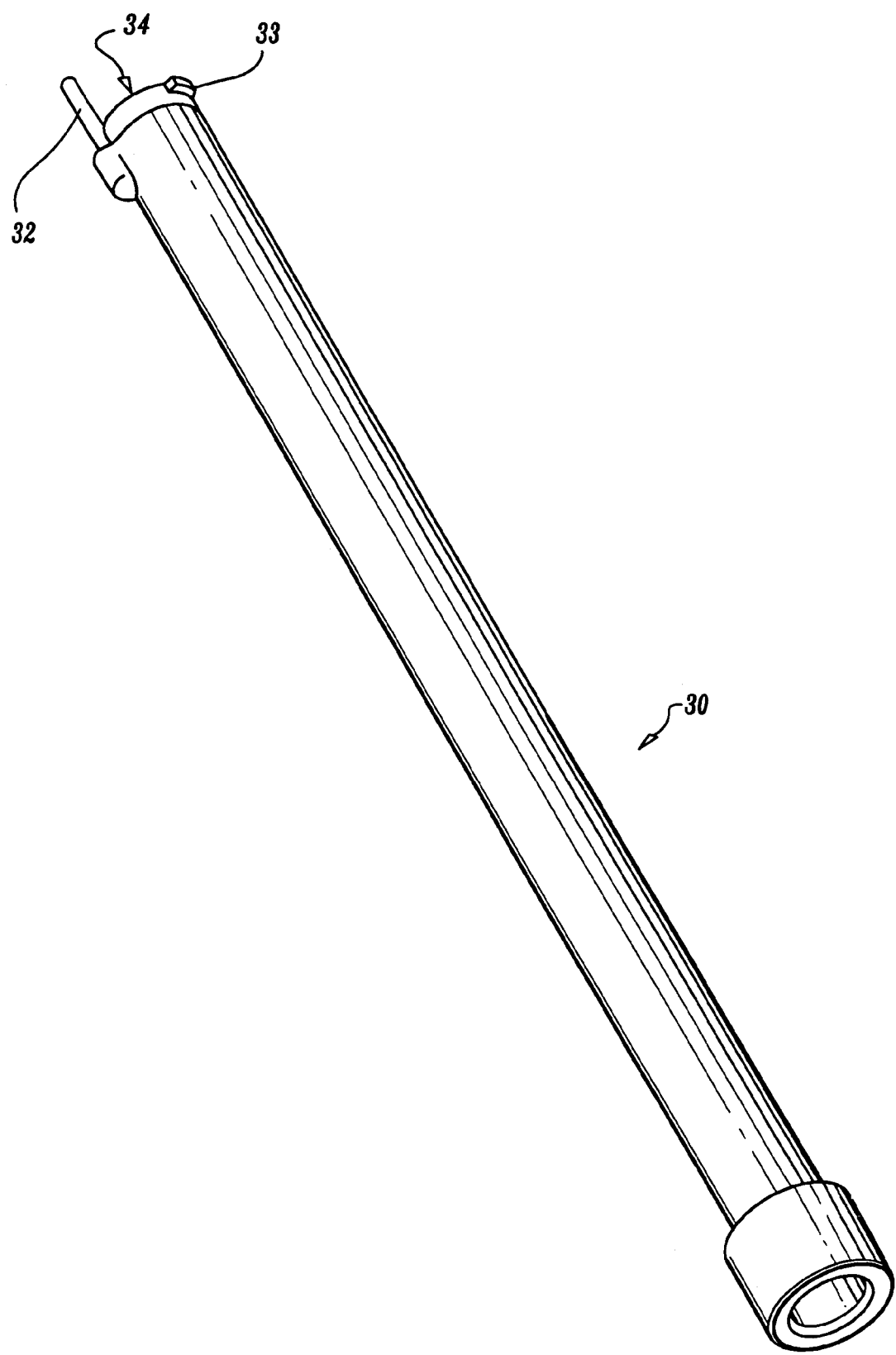
FIG. 5 is a perspective view of the guide of the present disclosure.
Figure 6:
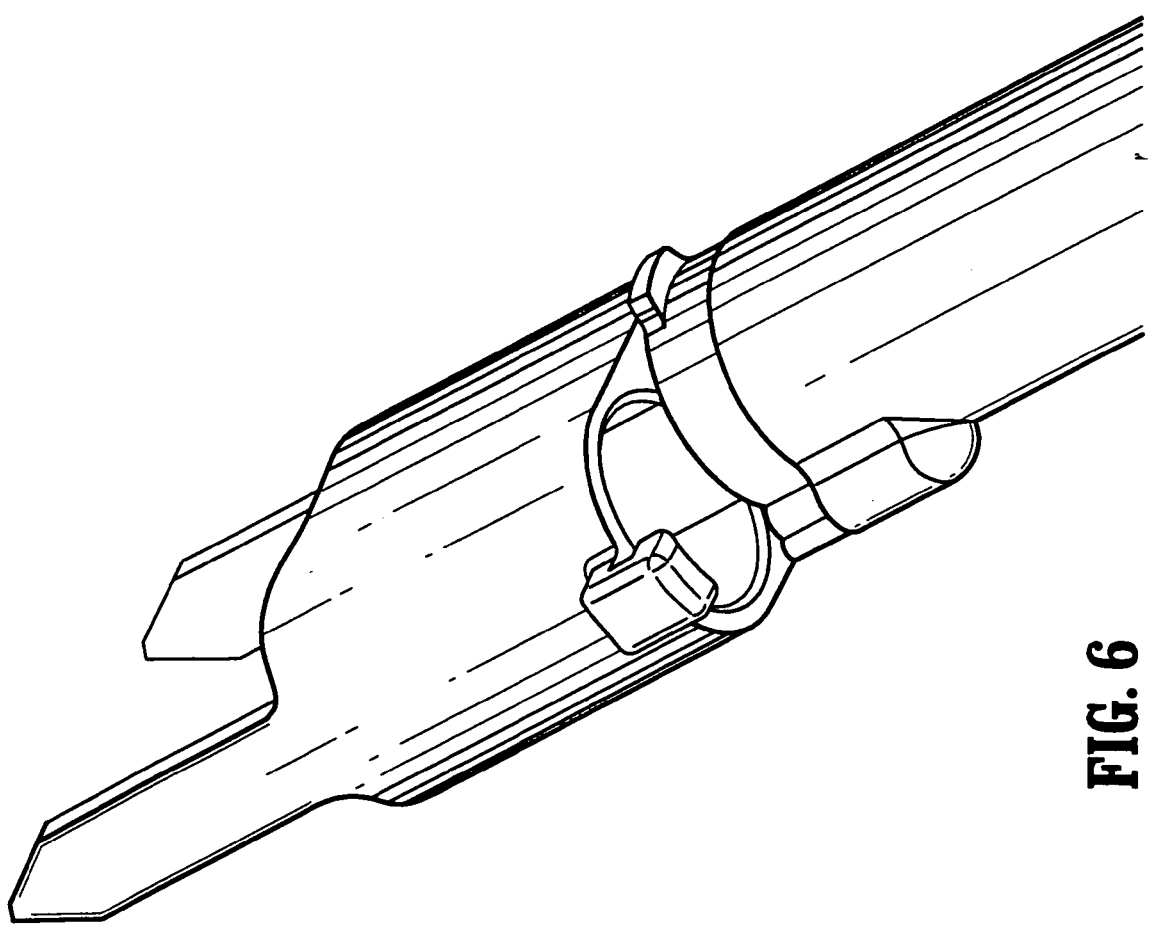
FIG. 6 is a perspective view illustrating attachment of the guide to the tang retractor.

The fusion cage (10) disclosed herein can be implemented with another fusion cage to reduce the total amount of space occupied by two conventional fusion cages placed side by side. The fusion cage (10) has a helical thread (14) for facilitating insertion and securing of the cage (10) in a vertebral disc space. The thread (14) is carved out to form concave portions (16, 17) to reduce the profile of the thread. As shown, the concave portions (16, 17) are preferably provided 180 degrees apart. If desired, only one concave portion is necessary to carry out the present invention. It is possible, also, to provide more than two concave portions if desired. The concave portions (16, 17) allow two or more cages (10, 11) to be placed close together as the radiused portion of one cage (11) is placed within the concave portion (17) of an adjacent cage (10), as shown in FIG. 3*b*. As can be appreciated, the combined width (transverse space) of the two low profile cages (10, 11) placed in this fashion is less than the combined width if two conventional cages without at least one of them having a concave portion were placed side by side.

FIGS. 4–7*b* illustrate an insertion instrument set for fusion cages according to the present invention. The instrument set includes a tang retractor (20), a guide (30) and an impactor (40) and impactor plate (41). The tang retractor (20) includes a pair of spaced apart tangs (21) which are dimensioned and configured as wedges at the distal end for insertion into and distraction of the disc space. The configuration of the tangs (21) and the manner in which they distract the disc space is described in pending U.S. patent application Ser. No. 08/889,661, filed Jul. 8, 1997, the contents of which are incorporated herein by reference.

The tang retractor (20) includes a pair of proximally extending slotted tabs (22) for mounting the tabs (42) of the impactor plate (41) when the impactor plate (41) is mounted to the proximal end of the distractor (20). The tabs (42) are inserted into the slots (23) of the tabs (22) to mount the impactor plate (41) and the elongated integral impactor (40), which is connected to the impactor plate (41) by threads (43, 45), to the tang retractor (20). The impactor (40) can then be impacted or tapped at its proximal end (47) by a suitable tool, such as a hammer, to insert the tang (21) into a vertebral space. After insertion, the tabs (42) are slid out of engagement with slots (23) to separate and remove the impactor (40) and impactor plate (41), leaving the tang retractor (20) in place with the tangs (21) inserted in the vertebral space.

The guide (30) is then attached to tang retractor (20) by inserting the distal end pin (32) into the longitudinal slot (25) of the retractor (20). The distal end pin (32) is seated within the slot (25) 50 that the guide (30) can be pivoted, about the pin (32), with respect to the fixed tang retractor (20) between alignment with each of the two openings (26, 27) of the tang retractor (20), respectively. Each of the openings (26, 27) is configured to receive a fusion cage along with a conventional cage insertion tool (not shown). The guide (30) is rotated about pin (32) 50 that its axial bore (34) is aligned with one of the openings (26, 27) of the tang retractor (20) during hole preparation through a respective one of the openings. Suitable tools, such as those described in the aforementioned application Ser. No. 08/889,661, are inserted through the bore (34) to prepare the space for fusion cage insertion. Fusion cages such as the type of the present invention, are then inserted via an elongated insertion tool through the bore (34) and the respective tang retractor opening (26, 27) for placement within the vertebral space. Each cage is placed so that one of the concave portions (16, 17) faces the adjacent opening or bore in the vertebral space. The guide (30) is subsequently rotated so that axial bore (34) is aligned with the other opening (26, 27) in the retractor 20. Another fusion cage, either with or without concave portions, is inserted in a similar manner as described above so that its outer circumferential portion fits within the concave portion (16, 17) of the first-inserted fusion cage.

It is contemplated that an interlocking device (33) be provided to retain the guide (30) in each of its two aligned positions relative to the tang retractor (20) during site preparation and insertion of a fusion cage therethrough.

Alternate embodiments of the present invention, such as those shown in FIGS. 8–9, include variously configured implant bodies having a concave portion to facilitate close, adjacent placement with additional implant bodies. For instance, the implant body (100) in FIG. 8 is a half-oval having a central opening (102) to facilitate bone fusion, and a concave side wall (104) configured to matingly receive a circumferential, convex wall (106) of an adjacent, oval implant (108). The implant body (200) of FIG. 9, is generally cylindrical and has a concave channel (202) aligned generally perpendicularly to a longitudinal axis running between open ends (204, 206).

It can be appreciated that the tang retractor (20) having a length approximately equal to its width increases visibility as well as enables the user to more easily remove extraneous disc tissue because of the increased mobility of instruments, e.g. rongeurs, inserted through the retractor 20. While this is the preferred embodiment, the length of the retractor (20) may be varied as desired to achieve different advantages.

While the preferred embodiment has been disclosed herein, it is understood and contemplated that modifications and variations may be employed without departing from the scope of the present invention.

The invention claimed is:

1. A bone fusion implant system comprising:
a first implant body having flat top and bottom surfaces for engaging opposing vertebrae and a side wall extending between said flat top and bottom surfaces, said side wall having an outer surface with a concave recess;
a second implant body having flat top and bottom surfaces for engaging the opposing vertebrae and a side wall extending between said flat top and bottom surfaces, said side wall of said second implant body having an outer surface defining at least one convex curve, said convex curve being receivable within said concave recess of said first implant body for nesting said first and second implant bodies in side-by-side relation between said opposing vertebrae, wherein said first and second implant bodies have different shapes.

2. The system as claimed in claim 1, wherein said top and bottom surfaces of said first and second implant bodies are devoid of projections.

3. The system as claimed in claim 1, wherein said first implant body has a half oval shape.

4. The system as claimed in claim 1, wherein said second implant body has an oval shape.

5. The system as claimed in claim 1, wherein said first and second implants include central openings adapted for receiving bone growth inducing substances.

6. A bone fusion implant system comprising:
a first implant body having flat top and bottom surfaces for engaging opposing vertebrae and a side wall extending between said flat top and bottom surfaces, said side wall having an outer surface with a concave recess;
a second implant body having flat top and bottom surfaces for engaging the opposing vertebrae and a side wall extending between said flat top and bottom surfaces, said side wall of said second implant body having an outer surface defining at least one convex curve, said convex curve being receivable within said concave recess of said first implant body for nesting said first and second implant bodies in side-by-side relation between said opposing vertebrae, wherein said first and second implant bodies have different sizes.

7. A bone fusion implant system comprising:
a first implant body having substantially flat top and bottom surfaces adapted for engaging opposing vertebrae and a side wall extending between said top and bottom surfaces, said side wall having an outer surface with a concave recess;
a second implant body having substantially flat top and bottom surfaces adapted for engaging the opposing vertebrae and a side wall extending between said top and bottom surfaces thereof, said side wall of said second implant body having an outer surface defining a convex curve extending continuously around a perimeter of said second implant body, wherein any section of the convex curve is receivable within the concave recess of said first implant body for nesting said first and second implant bodies in side-by-side relation between said opposing vertebrae.

8. The system as claimed in claim 7, wherein said first and second implant bodies are different sizes.

9. The system as claimed in claim 7, wherein said second implant body is larger than said first implant body.

10. The system as claimed in claim 7, wherein said first implant body is a half-oval and said second implant body is an oval.

11. The system as claimed in claim 7, wherein said first and second implant bodies are different shapes.

12. The system as claimed in claim 7, wherein said top and bottom surfaces of said first implant body are parallel to one another and said top and bottom surfaces of said second implant body are parallel to one another.

13. The system as claimed in claim 7, wherein said top and bottom surfaces of said first and second implant bodies are devoid of projections.

* * * * *